US012649042B2

(12) United States Patent
Lee et al.

(10) Patent No.: US 12,649,042 B2
(45) Date of Patent: Jun. 9, 2026

(54) HEAD-MOUNTED DEVICE FOR REDUCING SYMPTOMS OF CYBERSICKNESS

(71) Applicant: National Tsing Hua University, Hsinchu City (TW)

(72) Inventors: Yun-Ju Lee, Hsinchu City (TW); Yu-Jung Chen, Hsinchu City (TW)

(73) Assignee: NATIONAL TSING HUA UNIVERSITY, Hsinchu City (TW)

( * ) Notice: Subject to any disclaimer, the term of this patent is extended or adjusted under 35 U.S.C. 154(b) by 979 days.

(21) Appl. No.: 17/857,559

(22) Filed: Jul. 5, 2022

(65) Prior Publication Data

US 2023/0310791 A1 Oct. 5, 2023

(30) Foreign Application Priority Data

Mar. 16, 2022 (TW) .................................. 111109557

(51) Int. Cl.
*A61M 21/00* (2006.01)

(52) U.S. Cl.
CPC ..... *A61M 21/00* (2013.01); *A61M 2021/0022* (2013.01); *A61M 2209/088* (2013.01); *A61M 2210/06* (2013.01)

(58) Field of Classification Search
None
See application file for complete search history.

(56) References Cited

U.S. PATENT DOCUMENTS

| | | | | |
|---|---|---|---|---|
| 6,783,237 B1 * | 8/2004 | Jeannin | .................... | G02C 7/00 |
| | | | | 351/158 |
| 2012/0016431 A1 * | 1/2012 | Paul | ................... | A61N 1/36535 |
| | | | | 607/2 |
| 2013/0123656 A1 * | 5/2013 | Heck | ..................... | A63F 13/235 |
| | | | | 463/36 |
| 2015/0273179 A1 * | 10/2015 | Krueger | ................. | G02C 11/00 |
| | | | | 600/27 |
| 2020/0166742 A1 | 5/2020 | Peyman | | |
| 2020/0390997 A1 * | 12/2020 | Jovanov | ................... | A61B 5/16 |

FOREIGN PATENT DOCUMENTS

| | | |
|---|---|---|
| CN | 112363618 A | 2/2021 |
| TW | 202005690 A | 2/2020 |

* cited by examiner

*Primary Examiner* — Thaddeus B Cox

(74) *Attorney, Agent, or Firm* — Birch, Stewart, Kolasch & Birch, LLP

(57) ABSTRACT

A head-mounted device for reducing symptoms of cyber-sickness includes a main shell, and a stimulation unit. The main shell includes first, second and third tube bodies that are arc-shaped and that are worn respectively on the top and back of the user's head and the user's ear. The stimulation unit includes first, second and third components that are received respectively in the first, second and third tube bodies, that are movable in a rolling, sliding or flowing manner with low friction, and that are configured to generate and transmit a stimulation force, through one end of the respective one of the first, second and third tube bodies, to the use's vestibular system in respond to movement of the user's head.

5 Claims, 5 Drawing Sheets

First Stage closed tube          steel balls (mass = m)

Second Stage

Third Stage

HEAD-MOUNTED DEVICE FOR REDUCING SYMPTOMS OF CYBERSICKNESS

CROSS-REFERENCE TO RELATED APPLICATION

This application claims priority of Taiwanese Patent Application No. 111109557, filed on Mar. 16, 2022.

FIELD

The disclosure relates to a head-mounted device, and more particularly to a head-mounted device for reducing symptoms of cybersickness.

BACKGROUND

With the rising popularity of virtual reality (VR) or augmented reality (AR) head-mounted displays, an increasing number of users have reported experiencing cybersickness, which is a form of motion sickness occurring as a result of exposure to VR or AR environments. Specifically, cybersickness is presumed to occur when a user's perception of self-motion based on visual inputs from a VR or AR device is at odds with that based on sensory inputs from the user's vestibular system (i.e., when what is perceived visually does not match with what is perceived by the vestibular system). As a result, symptoms such as pallor, headache, and dizziness, are often induced.

In order to reduce the symptoms of cybersickness, an existing method proposed to reduce the above-mentioned visual-vestibular conflicts by changing the displayed content of the head-mounted display. However, such method can detract from the intended VR or AR effect of the head-mounted display, thus lowering its value in the entertainment industry or affecting its ability in delivering information with precision in the medical or educational field.

In addition, an existing control system with the same objective proposed to control a motor based on movement of the user's head, so that the motor drives a stimulating object (e.g., a tapping object) to stimulate the user's vestibular system. However, since such control system needs to perform system calculations before transmitting signals to the motor, a time delay is perceivable by the user which can compromise the stimulation effect of the system in reducing the visual-vestibular conflicts.

SUMMARY

Therefore, the object of the disclosure is to provide a head-mounted device that can alleviate at least one of the drawbacks of the prior art.

According to the disclosure, the head-mounted device for reducing symptoms of cybersickness is adapted to be worn on a user's head and to be used cooperatively with a head-mounted display. The head-mounted device includes a main shell and a stimulation unit.

The main shell is adapted to be mounted on the user's head, and includes a first tube body, a second tube body and a third tube body that are adapted to be respectively disposed at the top of the user's head, the back of the user's head and one of the user's ears. The first, second and third tube bodies are arc-shaped, have arc-shaped central axes which respectively define imaginary first, second and third planes, and are fixedly connected to one another in a manner that the first, second and third planes are perpendicular to one another. Each of the first, second and third tube bodies has opposite closed ends. For each of the first and second tube bodies, each of the closed ends is adapted to be disposed proximal to a respective one of the user's ears.

The stimulation unit includes a first component, a second component and a third component. Each of the first, second and third components is received in a respective one of the first, second and third tube bodies, and is configured to be movable in at least one of rolling, sliding and flowing manners with low friction in the respective one of the first, second and third tube bodies.

When rotation of the user's head drives at least one of the first, second and third components of the stimulation unit to move in the respective one of the first, second and third tube bodies, the at least one of the first, second and third components is adapted to generate and transmit a stimulation force, through one of the closed ends of the respective one of the first, second and third tube bodies, to the user's vestibular system for stimulating the user's vestibular perception.

When the at least one of the first, second and third components is composed of at least one rigid body, the stimulation force is proportional to an angular acceleration of the user's head, a total mass of the at least one rigid body, and a radius of curvature of the respective one of the first, second and third tube bodies.

When the at least one of the first, second and third components is composed of a fluid, the stimulation force is proportional to the angular acceleration of the user's head, the radius of curvature of the respective one of the first, second and third tube bodies, an inner cross-sectional area of the respective one of the first, second and third tube bodies, and a density of the fluid.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Figure 1:
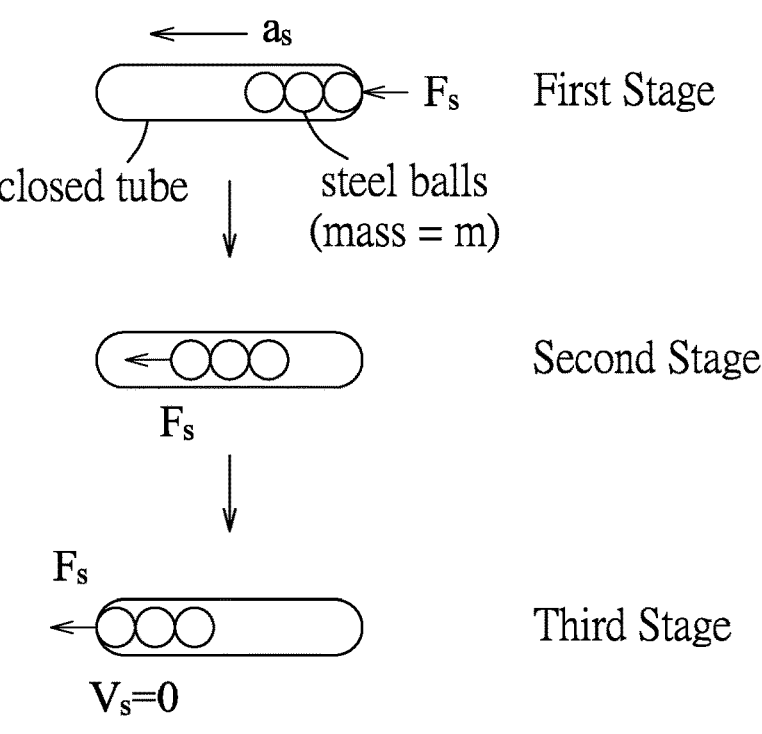
FIG. 1 is a schematic diagram illustrating momentum transferring among a closed tube and a plurality of steel balls disposed in the closed tube.

Before the present disclosure is described in greater detail, it should be noted that where considered appropriate, reference numerals or terminal portions of reference numerals have been repeated among the figures to indicate corresponding or analogous elements, which may optionally have similar characteristics.

Figure 2:
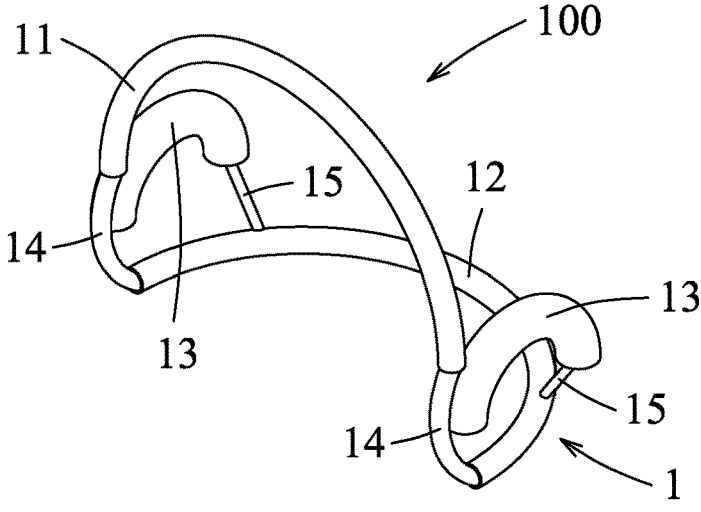
FIG. 2 is a perspective view illustrating an embodiment of a head-mounted device for reducing symptoms of cybersickness according to the disclosure.
Figure 3:
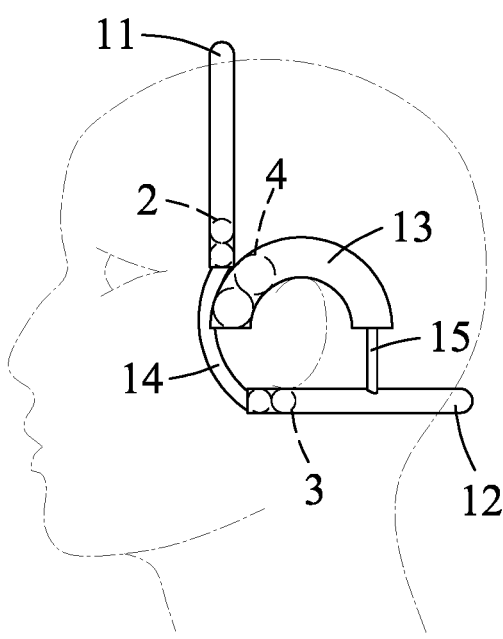
FIG. 3 is a schematic side view illustrating the embodiment being worn on a user's head.
Figure 4:
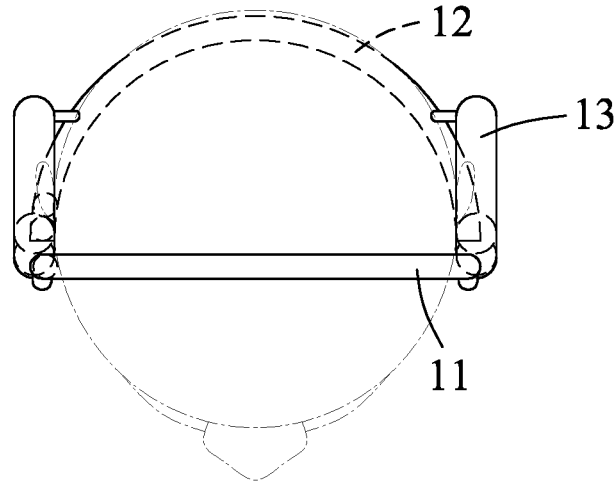
FIG. 4 is a schematic top view illustrating the embodiment being worn on the user's head.

Referring to FIGS. 2 to 4, a head-mounted device 100 for reducing symptoms of cybersickness according to the disclosure is adapted to be worn on a user's head and to be used cooperatively with a VR or AR head-mounted display (not shown). When in use, the head-mounted device 100 counteracts visual-vestibular conflicts induced by the head-mounted display by applying physical stimulation to the user's vestibular system in response to motions of the user's head (e.g., tilting, turning, nodding, or a combination thereof) to stimulate the user's vestibular perception, thereby reducing symptoms of cybersickness. The head-mounted device 100 includes a main shell 1 and a stimulation unit.

Figure 8:
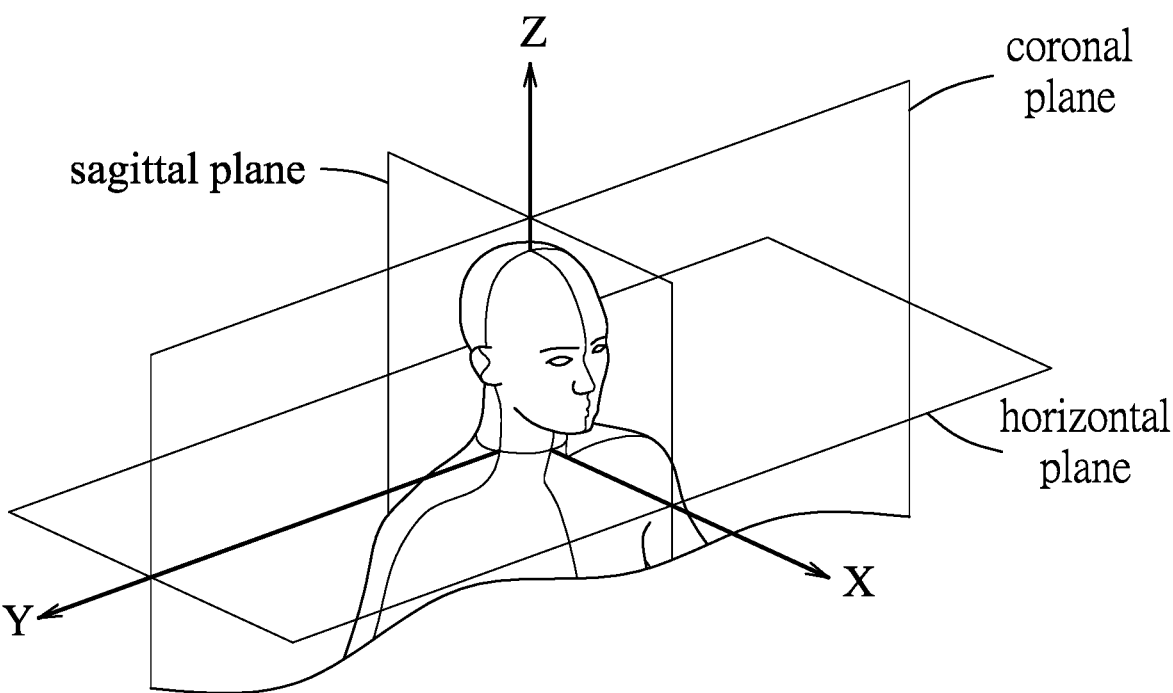
FIG. 8 is a schematic diagram illustrating the anatomical coronal, sagittal, and horizontal planes of the user's body defined in reference to a coordinate system.

Referring to FIG. 8, for the purpose of explanation, three principle anatomical planes of the user's body (i.e., coronal, sagittal, and horizontal planes) are defined hereafter in reference to a coordinate system having X-, Y- and Z-axes. Specifically, the coronal plane that divides the user's head into front and rear portions is defined by an Y-Z plane of the coordinate system. The sagittal plane that divides the user's head into left and right portions is defined by an X-Z plane of the coordinate system. The horizontal plane that that is perpendicular to the coronal and sagittal planes and that is disposed at same level as the user's neck is defined by an X-Y plane of the coordinate system.

In the present embodiment, movement of the user's head includes at least one of the following: roll movement (i.e., a head tilt towards either of the shoulders) about a first axis (not shown) parallel to the X-axis; yaw movement (i.e., a side-to-side head rotation) about a second axis (not shown) parallel to the Z-axis; and pitch movement (i.e., a downward or upward head tilt) about a third axis (not shown) parallel to the Y-axis.

The configurations and operation of the head-mounted device 100 are described hereinafter in reference to when the head-mounted device 100 is worn on the user's head.

The main shell 1 is adapted to be mounted on the user's head with aid of a fastening strap (not shown), and includes an arc-shaped first tube body 11, an arc-shaped second tube body 12 and two arc-shaped third tube bodies 13. In the present embodiment, each of the first, second and third tube bodies 11, 12, 13 is semicircular and provided with a circular inner cross-section, but is not limited thereto in variations of the embodiment.

As shown in FIG. 2, the first tube body 11 is adapted to be disposed at the top of the user's head. The second tube body 12 is adapted to be disposed at the back of the user's head. The third tube bodies 13 are adapted to be disposed at the user's ears, respectively. Each of the first, second and third tube bodies 11, 12, 13 has opposite closed ends. For each of the first and second tube bodies 11, 12, each of the closed ends is adapted to be disposed proximal to a respective one of the user's ears. For each of the third tube bodies 13, one of the closed ends is connected to a respective one of the closed ends of the first tube body 11.

The main shell 1 further includes two first fixing members 14 that are connected between the first and second tube bodies 11, 12, and two second fixing members 15 that are connected between the second and third tube bodies 12, 13. Specifically, each of the first fixing members 14 has one end connected to a respective one of the close ends of the first tube body 11, and an opposite end connected to a respective one of the close ends of the second tube body 12. Each of the second fixing members 15 has one end connected to one of the close ends of a respective one of the third tube bodies 13, and an opposite end connected to a segment of the second tube body 12 proximal to a respective close end of the second tube body 12.

The first and second tube bodies 11, 12 have arc-shaped central axes that respectively define imaginary first and second planes. The third tube bodies 13 have arc-shaped central axes that respectively define imaginary third and fourth planes which are parallel to each other. The first, second and third tube bodies 11, 12, 13 are fixedly connected to one another by the first and second fixing members 14, 15 in a manner that the first and second planes are perpendicular to each other and to the third and fourth planes.

It should be noted that, referring to FIG. 3 in conjunction with FIG. 8, the first plane is parallel to the coronal plane (or may be coplanar with the coronal plane in variations of the embodiment). The second plane is parallel to the horizontal plane. The third and fourth planes are parallel to the sagittal plane.

It should also be noted that a radius of curvature of each of the first, second and third tube bodies 11, 12, 13 is determined based on a database of two-dimensional head sizes of users.

In variations of the embodiment, the main shell 1 may include only one third tube body 13, one first fixing member 14 and one second fixing member 15. In addition, in these variations, each of the first, second and third tube bodies 11, 12, 13 may has a semicircular or U-shaped inner cross section.

Referring again to FIGS. 2 and 3, in the present embodiment, the stimulation unit includes a first component 2, a second component 3 and two third components 4. Each of the first and second components 2, 3 is movably received in a respective one of the first and second tube bodies 11, 12. Each of the third components 4 is movably received in a respective one of the third tube bodies 13. In variations of the embodiment, in which the main shell 1 includes only one third tube body 13, the stimulation unit may include only one third component 4.

Specifically in the present embodiment, each of the first, second and third components 2, 3, 4 is configured to be movable in at least one of rolling, sliding and flowing manners with low friction in the respective one of the first, second and third tube bodies 11, 12, 13.

When the user's head rotates while watching images of the head-mounted display, rotation of the user's head drives at least one of the first, second and third components 2, 3, 4 of the stimulation unit to move in the respective one of the first, second and third tube bodies 11, 12, 13, and the at least one of the first, second and third components 2, 3, 4 is adapted to generate and transmit a stimulation force, through one of the closed ends of the respective one of the first, second and third tube bodies 11, 12, 13, to the user's vestibular system for stimulating the user's vestibular perception.

Before an operation of the head-mounted device 100 is described in detail hereafter, please refer to FIG. 1, which illustrates the physical principle of motion to which operation of the head-mounted device 100 accords. Specifically, FIG. 1 illustrates momentum transferring among an elongated closed tube that has a circular cross-section, and a plurality of steel balls (whose total mass is designated by m) that are disposed in the closed tube. The momentum transferring process is divided into three stages: a first stage, a second stage and a third stage.

In the first stage, when a right end of the closed tube is subjected to an external force $F_s$, the closed tube and the steel balls move together toward the left at an acceleration as. In this case, according to Newton's second law of motion, the steel balls gain a momentum during the movement, and exerts an equal amount of reaction force $F_s$ on the closed tube, wherein $$F_s = m \times a_s.$$

In the second stage, after the external force is removed and the closed tube stops moving, the momentum of the steel balls drives the steel balls to continue moving toward the left at a constant velocity $V_s$ (it should be noted that, in this case, a friction force is nearly negligible so that rolling resistance is ignored). Given the steel balls are driven by the closed tube over a duration of time $t_1$, an impulse of the steel balls is $F_s \times t_1 = m \times \Delta V$, wherein $m \times \Delta V$ is a change in the momentum of the steel balls, and $\Delta V$ is a change in the velocity of the steel balls relative to the closed tube from the time the steel balls start to move with the closed tube (i.e., relative velocity is zero) to the time they move relative to the closed tube at the constant velocity $V_s$, and the momentum of the steel balls is $m \times V_s$.

Finally, in the third stage, the steel balls hit a left end of the closed tube and transfer their momentum to the closed tube until they no longer move relative to the closed tube. In this case, given a duration of time that the steel balls hit the closed tube until fully stopped (i.e., the velocity of the steel balls changes from $V_s$ to 0) is $t_2$, and a change in the velocity of the steel balls is $\Delta V = (V_s - 0) = V_s$, a change in the momentum of the steel balls (i.e., $m \times V_s$) is equal to an impulse of the steel balls applied to the closed tube, that is, $m \times V_s = F_B \times t_2$, where $F_B$ is a force exerted by the steel balls on the closed tube. As such, the force of the steel balls can be obtained as $$F_B = m \times \frac{V_s}{t_2}.$$

In view of the above, when each of the first, second and third components 2, 3, 4 is composed of at least one rigid body (i.e., the steel balls shown in FIG. 3, but not limited thereto in variations of the embodiment), the stimulation force is proportional to an angular acceleration of the user's head, a total mass of the at least one rigid body, and a radius of curvature of the respective one of the first, second and third tube bodies 11, 12, 13.

In addition, the above-mentioned physical principle of motion can be applied to any of the following combinations: a combination of the first tube body 11 and the first component 2; a combination of the second tube body 12 and the second component 3; and a combination of each of the third tube bodies 13 and the respective one of the third components 4. Application of the motion principle for each of the afore-mentioned combinations is described in detail hereinafter with reference to FIGS. 5 to 7.

Figure 5:
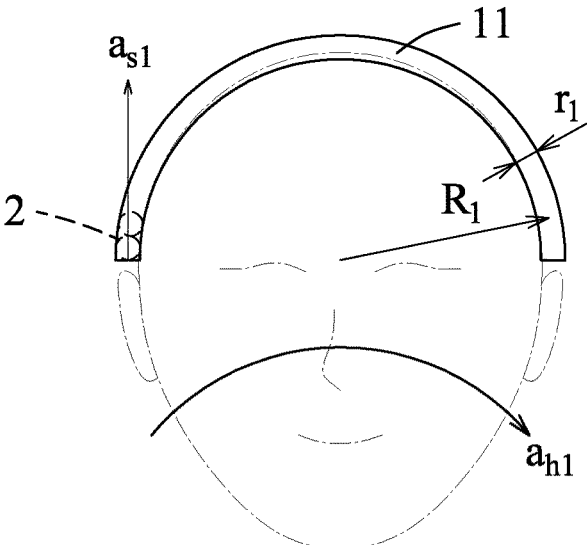
FIG. 5 is a schematic front view illustrating a movement relationship between a first tube body and a first component of the embodiment when the user's head tilts to the left.

Referring to FIG. 5, when the user's head tilts toward the right side of the drawing (i.e., toward the user's left shoulder), it rotates about the first axis (in a clockwise direction as shown in the drawing). Given an angular acceleration of rotation is $\alpha_{h1}$, a tangential acceleration $a_{s1}$ in an upward tangential direction of the first tube body 11 is generated by the angular acceleration $\alpha_{h1}$, and is obtained as $a_{s1} = R_1 \times \alpha_{h1}$, wherein $R_1$ is a radius of curvature of the first tube body 11. Therefore, according to Newton's second law of motion, the stimulation force applied by the first component 2 to the user's vestibular system can be obtained as $F_1 = m_1 \times R_1 \times \alpha_{h1}$, wherein $m_1$ is a mass of the first component 2.

Figure 6:
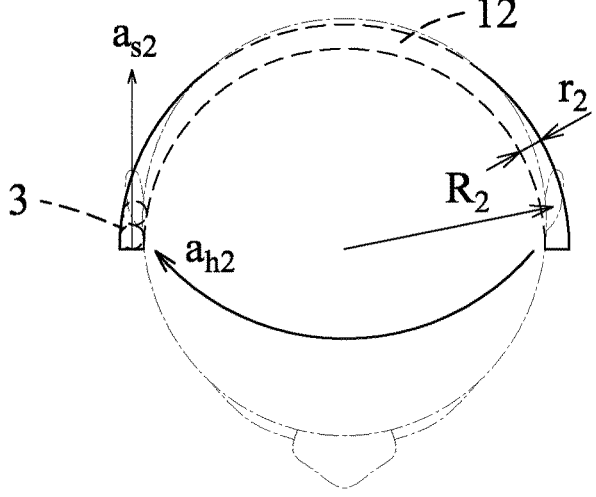
FIG. 6 is a schematic top view illustrating a movement relationship between a second tube body and a second component of the embodiment when the user's head rotates in clockwise direction.

Similarly, referring to FIG. 6, when the user's head rotates toward the right about the first axis (in a clockwise direction as shown in the drawing). Given an angular acceleration of rotation is $\alpha_{h2}$, a tangential acceleration $a_{s2}$ in a rearward tangential direction of the second tube body 12 is generated by the angular acceleration $\alpha_{h2}$, and is obtained as $a_{s2} = R_2 \times \alpha_{h2}$, wherein $R_2$ is a radius of curvature of the second tube body 12. Therefore, according to Newton's second law of motion, the stimulation force applied by the second component 3 to the user's vestibular system can be obtained as $F_2 = m_2 \times R_2 \times \alpha_{h2}$, wherein $m_2$ is a mass of the second component 3.

Figure 7:
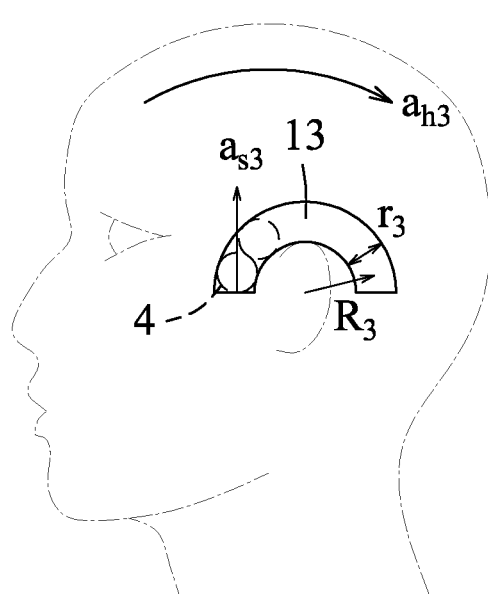
FIG. 7 is a schematic side view illustrating a movement relationship between a third tube body and a third component of the embodiment when the user's head 20 tilts backward.

Similarly, referring to FIG. 7, when the user's head tilts backwards, it rotates about the third axis (in a clockwise direction as shown in the drawing). Given an angular acceleration of rotation is $\alpha_{h3}$, a tangential acceleration $a_{s3}$ in an upward tangential direction of each of the third tube bodies 13 (only one is shown) is generated by the angular acceleration $\alpha_{h3}$, and is obtained as $a_{s3} = R_3 \times \alpha_{h3}$, wherein $R_3$ is a radius of curvature of the third tube bodies 13. Therefore, according to Newton's second law of motion, the stimulation force applied by each of the third components 4 (only one is shown) to the user's vestibular system can be obtained as $F_3 = m_3 \times R_3 \times \alpha_{h3}$, wherein $m_3$ is a mass of each of the third components 4.

Given an effective vestibular stimulation force is, for example, 0.225 kg (or $0.225 \times 9.8 = 2.205$ N), a referential angular acceleration range of human head rotation, for example, 0.1-0.5 krad/s$^2$, and radii of curvature fitting for the human head, $R_1 = R_2 = 90$ mm and $R_3 = 30$ mm, the mass of each of the first, second and third components 2, 3, 4, that is, $m_1$, $m_2$ and $m_3$, can be determined. For example, according to $a_{s1} = R_1 \times \alpha_{h1}$, $a_{s2} = R_2 \times \alpha_{h2}$ and $a_{s3} = R_3 \times \alpha_{h3}$, the following results are yielded:

a value range of $a_{s1}$ is $(90 \times 0.1)$ m/s$^2$ to $(90 \times 0.5)$ m/s$^2$, i.e., 9-45 m/s$^2$;

a value range of $a_{s2}$ is $(90 \times 0.1)$ m/s$^2$ to $(90 \times 0.5)$ m/s$^2$, i.e., 9-45 m/s$^2$; and a value range of $a_{s3}$ is $(30 \times 0.1)$ m/s$^2$ to $(30 \times 0.5)$ m/s$^2$, i.e., 3-15 m/s$^2$.

In addition, based on the value ranges of $a_{s1}$, $a_{s2}$ and $a_{s3}$, the following results are yielded:

a value range of $m_1$ is 2.205/45 kg to 2.205/9 kg, i.e., 49-245 g;

a value range of $m_2$ is 2.205/45 kg to 2.205/9 kg, i.e., 49-245 g; and a value range of $m_3$ is 2.205/15 kg to 2.205/3 kg, i.e., 147-735 g.

Therefore, the head-mounted device 100 can be designed based on the above results to generate effective stimulation forces.

Figure 9:
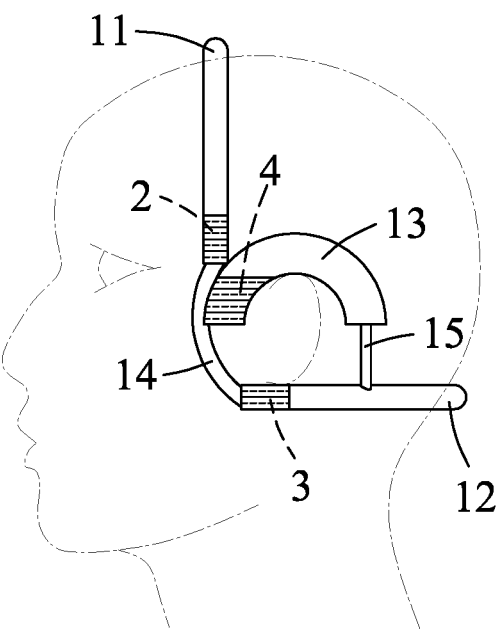
FIG. 9 is a schematic side view illustrating a variation of the embodiment being worn on a user's head.

Further, referring to FIG. 9, in a variation of the embodiment, when each of the first, second and third components 2, 3, 4 is composed of a fluid, the stimulation force is proportional to the angular acceleration of the user's head, the radius of curvature of the respective one of the first, second and third tube bodies 11, 12, 13, an inner cross-sectional area of the respective one of the first, second and third tube bodies 11, 12, 13, and a density of the fluid.

In this case, Newton's second law of motion can be applied in conjunction with Bernoulli's principle with the following equation:

$$P_1 + \frac{1}{2}\rho v_1^2 = P_2 + \frac{1}{2}\rho v_2^2,$$

wherein $\rho$ is the density of the fluid. Specifically, referring again to FIG. 1, assuming the fluid in the closed tube is pushed by the closed tube in the first stage and generates the impulsive force in the second stage, and assuming a fluid pressure applied to the right end of the closed tube in the second stage is $P_1=0$ with a flow velocity of $v_1=V$, and a fluid pressure applied to the left end of the closed tube is $P_2=P$ with a flow velocity of $v_2=0$. Then, since a fluid force applied by the fluid to the closed tube in the third stage can be obtained as $$F = P_2 \times A = \frac{\rho V^2}{2} \times \pi r^2,$$

wherein A is an internal cross-sectional area of the closed tube and r is an inner radius of the closed tube, the fluid forces corresponding respectively to FIGS. 5 to 7 (i.e., $F_1$, $F_2$ and $F_3$) can be obtained by the equation $$F = \frac{\rho V^2}{2} \times \pi r^2$$

as follow:

$$F_1 = \frac{1}{2}\left(\pi r_1^2 \rho_1 V_1^2\right),$$

wherein $r_1$ is an inner radius of the first tube body 11, $\rho_1$ is a density of the first component 2 (i.e., density of fluid in the first tube body 11), and $V_1$ is a tangential velocity of the first tube body 11;

$$F_2 = \frac{1}{2}\left(\pi r_2^2 \rho_2 V_2^2\right),$$

wherein $r_2$ is an inner radius of the second tube body 12, $\rho_2$ is a density of the second component 3 (i.e., density of fluid in the second tube body 12), and $V_2$ is a tangential velocity of the second tube body 12; and $$F_3 = \frac{1}{2}\left(\pi r_3^2 \rho_3 V_3^2\right),$$

wherein $r_3$ is an inner radius of each of the third tube bodies 13, $\rho_3$ is a density of each of the third components 4 (i.e., density of fluid in the third tube bodies 13), and $V_3$ is a tangential velocity of each of the third tube bodies 13.

Similarly, as mentioned above, given the effective vestibular stimulation force is 0.225 kg (or 2.205 N), maximum referential angular velocities of human head rotations are 12.6 rad/s (roll movement), 25 rad/s (yaw movement) and 17.4 rad/s (pitch movement), and radii of curvature fitting for the human head are $R_1=R_2=90$ mm and $R_3=30$ mm, a maximum upward tangential velocity of the first tube body 11 can be obtained as $V_1=0.09\times12.6=1.13$ m/s, a maximum backward tangential velocity of the second tube body 12 can be obtained as $V_2=0.09\times25=2.25$ m/s, and a maximum upward tangential velocity of each of the third tube bodies 13 can be obtained as $V_3=0.03\times17.4=0.52$ m/s. In addition, when each of the first, second and third components 2, 3, 4 is composed of the same fluid, such as water, with a density of $\rho_1=\rho_1=\rho_1=1000$ kg/m$^3$. Then, according to $$r_n = \sqrt{\frac{2F_n}{\pi \rho_n V_n^2}},$$

wherein n=1, 2, 3, the minimum inner radii of the first, second and third tube bodies 11, 12, 13 can be obtained as $r_1\approx10.6$ mm, $r_2\approx5.3$ mm and $r_3\approx23$ mm, respectively. As such, the head-mounted device 100 can be designed based on the above results to generate effective stimulation forces.

In summary, by virtue of the configurations of the main shell 1 and the stimulation unit, when the head-mounted device of the present disclosure is used cooperatively with the head-mounted display, kinetic energy generated by the movement of the user's head can be converted to a stimulation force and fed back through indirect means to a region of the user's head disposed near the vestibular system. As such, the additional sensory stimulation force provides stimulation user's vestibular system to counteract the visual-vestibular conflicts, thereby reducing the symptoms of cybersickness. Furthermore, compared with the prior art, the head-mounted device of the present disclosure does not require a control system to perform system calculations, and thus is able to ensure an immediate stimulation effect without any perceivable time delay.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A head-mounted device for reducing symptoms of cybersickness, adapted to be worn on a user's head and to be used cooperatively with a head-mounted display for stimulating a vestibular perception of a vestibular system of the user, said head-mounted device comprising:

a main shell adapted to be mounted on the user's head, and including a first tube body, a second tube body and a third tube body that are adapted to be respectively disposed at the top of the user's head, the back of the user's head and one of the user's ears, said first, second and third tube bodies being arc-shaped, having arc-shaped central axes which respectively define imagi-nary first, second and third planes, and being fixedly connected to one another in a manner that the first, second and third planes are perpendicular to one another, each of said first, second and third tube bodies having opposite closed ends, for each of said first and second tube bodies, each of said closed ends being adapted to be disposed proximal to a respective one of the user's ears; and a stimulation unit including a first component, a second component and a third component, each of said first, second and third components being received in a respective one of said first, second and third tube bodies, and being configured to be movable in at least one of rolling, sliding and flowing manners in the respective one of said first, second and third tube bodies;

wherein when rotation of the user's head drives at least one of said first, second and third components of said stimulation unit to move in the respective one of said first, second and third tube bodies, said at least one of said first, second and third components is adapted to generate and transmit a stimulation force, through one of said closed ends of the respective one of said first, second and third tube bodies, to the vestibular system of the user for stimulating the vestibular perception of the user;

wherein each of said at least one of said first, second and third components is composed of a rigid body or a fluid;

wherein when each of said at least one of said first, second and third components is composed of the rigid body, the stimulation force is proportional to an angular acceleration of the user's head, a total mass of the rigid body, and a radius of curvature of the respective one of said first, second and third tube bodies; and wherein when each of said at least one of said first, second and third components is composed of the fluid, the stimulation force is proportional to the angular accel-eration of the user's head, the radius of curvature of the respective one of said first, second and third tube bodies, an inner cross-sectional area of the respective one of said first, second and third tube bodies, and a density of the fluid.

2. The head-mounted device as claimed in claim 1, wherein each of said first, second and third tube bodies is semicircular, and has a circular inner cross section.

3. The head-mounted device as claimed in claim 1, wherein the first, second and third planes are adapted to be parallel, in terms of anatomy, to the coronal, horizontal and sagittal planes of the user, respectively.

4. The head-mounted device as claimed in claim 3, wherein:

said main shell further includes an additional third tube body that is fixedly connected to said first and second tube bodies, that is adapted to be disposed at the other one of the user's ears, and that defines an imaginary fourth plane adapted to be parallel to the sagittal plane of the user; and said stimulation unit further includes an additional third component that is received in said additional third tube body, and that is configured to be movable in at least one of rolling, sliding and flowing manners in said additional third tube body.

5. The head-mounted device as claimed in claim 1, wherein the rigid body includes a plurality of steel balls.

* * * * *